(12) United States Patent
Dershem et al.

(10) Patent No.: US 7,517,925 B2
(45) Date of Patent: *Apr. 14, 2009

(54) BENZOXAZINES, THERMOSETTING RESINS COMPRISED THEREOF, AND METHODS FOR USE THEREOF

(75) Inventors: Stephen M. Dershem, San Diego, CA (US); Puwei Liu, San Diego, CA (US); Farhad G. Mizori, La Mesa, CA (US)

(73) Assignee: Henkel Corporation, Rocky Hill, CT (US)

( * ) Notice: Subject to any disclaimer, the term of this patent is extended or adjusted under 35 U.S.C. 154(b) by 417 days.

This patent is subject to a terminal disclaimer.

(21) Appl. No.: 10/735,119

(22) Filed: Dec. 11, 2003

(65) Prior Publication Data

US 2004/0123948 A1 Jul. 1, 2004

Related U.S. Application Data

(62) Division of application No. 10/008,591, filed on Nov. 13, 2001, now Pat. No. 6,743,852.

(51) Int. Cl.
*C08K 5/34* (2006.01)
(52) U.S. Cl. ........................................ 524/95; 428/457
(58) Field of Classification Search ................. 524/95; 428/457

See application file for complete search history.

(56) References Cited

U.S. PATENT DOCUMENTS

| | | | |
|---|---|---|---|
| 4,607,091 A | 8/1986 | Schreiber | 528/96 |
| 5,021,484 A | 6/1991 | Schreiber et al. | 524/100 |
| 5,200,452 A | 4/1993 | Schreiber | 524/398 |
| 5,443,911 A | 8/1995 | Schreiber et al. | 428/413 |
| 5,447,988 A | 9/1995 | Dershem et al. | 524/780 |
| 5,543,516 A | 8/1996 | Ishida | 544/69 |
| 6,034,194 A | 3/2000 | Dershem et al. | 526/262 |
| 6,034,195 A | 3/2000 | Dershem et al. | 526/262 |
| 6,207,786 B1 | 3/2001 | Ishida et al. | 528/94 |
| 6,906,120 B1 * | 6/2005 | Davis et al. | 523/436 |

OTHER PUBLICATIONS

Degani, "Novel Water-displacing Polymers Show Promise in Coating Uses," C&EN, Jul. 29, 1991, p. 20-22.

* cited by examiner

*Primary Examiner*—Kriellion A Sanders
(74) *Attorney, Agent, or Firm*—Steven C. Bauman

(57) ABSTRACT

In accordance with the present invention, there are provided novel benzoxazine compounds and thermosetting resin compositions prepared therefrom. Invention compositions are particularly useful for increasing adhesion at interfaces within microelectronic packages. Invention benzoxazines are useful for the preparation of invention compositions with properties which are associated with increased adhesion at interfaces, such as, for example, low shrinkage on cure and low coefficient of thermal expansion (CTE). In another aspect of the invention, there are provided die-attach pastes having increased interfacial adhesion. Invention die-attach pastes include benzoxazine-containing thermosetting resin compositions. In further aspects of the invention, there are provided methods for enhancing adhesive strength of thermosetting resin compositions and methods for enhancing adhesion of a substrate bound to a metallic surface by a thermosetting resin composition.

13 Claims, No Drawings

1

BENZOXAZINES, THERMOSETTING RESINS COMPRISED THEREOF, AND METHODS FOR USE THEREOF

FIELD OF THE INVENTION

The present invention relates to benzoxazines. In a particular aspect, the present invention relates to benzoxazine-containing thermosetting resin compositions. In yet another aspect, the present invention relates to compositions useful as adhesives for assembling electronic devices, as well as other applications, such as within the aerospace industry.

BACKGROUND OF THE INVENTION

Reliable performance of electronic devices depends primarily on the integrity of the microelectronic components contained therein. Most electronic devices contain several microchips which are housed in a variety of protective packages. These packages are composed of several distinct materials, each of which performs a specific function and contributes to the overall integrity of the package. For example, a typical ball-grid array (BGA) package contains, in addition to the substrate and microchip attached thereto, materials such as overmold adhesive, die-attach adhesive, and solder mask. The incorporation of all of these disparate materials into one package creates several adhesive interfaces within the package itself. In order to produce a reliable, long-lasting electronic device, the structural integrity of these interfaces must be maintained.

Interfacial adhesion is a critical parameter for the production of reliable microelectronic components. Materials with dissimilar coefficients of thermal expansion must be adhered via void-free bonds. The presence of any delamination in the final assembled product can lead to moisture entrapment within the void volume. The trapped moisture can be released "explosively" once the defective part is heated to solder reflow temperatures during final component assembly. The formation of sound adhesive bonds at the various interfaces present within a microelectronic package is therefore critical for the survival of that package during assembly. The formation of sound adhesive bonds is also necessary to insure a long service life for the final product.

Adhesive interfaces within electronic components are currently subjected to increasingly stringent processing conditions. For example, environmental concerns have resulted in a worldwide mandate to remove lead from all aspects of the microelectronic assembly process. The use of lead-free solder alloys, however, creates a new challenge for the reliable assembly of microelectronic components. The reflow temperatures required by lead-free alloys are several degrees higher than those containing lead. Soldering operations based on these new alloys generally must be conducted around 260° C., which is about forty degrees Celsius higher than had been previously required. The new, higher reflow temperatures place an extra strain on all of the adhesive interfaces within microelectronic packages. Indeed, strong adhesion at all of these interfaces is critical to the reliability of a microelectronic component.

Benzoxazines and compositions containing benzoxazines are known (see for example, U.S. Pat. Nos. 5,543,516 and 6,207,786 to Ishida, et. al.; S. Rimdusit and H. Ishida, "Development of New Class of Electronic Packaging Materials Based on Ternary Systems of Benzoxazine, Epoxy, and Phenolic Resins", *Polymer*, 41, 7941-49 (2000); and H. Kimura, et. al., "New Thermosetting Resin from Bisphenol A-based Benzoxazine and Bisoxazoline", *J. App. Polym. Sci.*, 72, 1551-58 (1999)). However, benzoxazines have generally not been used as components of thermosetting resin compositions to increase the interfacial adhesion thereof.

Accordingly, there is a need for compositions and methods which increase interfacial adhesion within microelectronic components.

SUMMARY OF THE INVENTION

In accordance with the present invention, there are provided novel benzoxazine compounds and thermosetting resin compositions prepared therefrom. Invention compositions are particularly useful for increasing adhesion at interfaces within microelectronic packages. Invention benzoxazines are useful for the preparation of invention compositions with properties which are associated with increased adhesion at interfaces, such as, for example, low shrinkage on cure and low coefficient of thermal expansion (CTE).

In another aspect of the invention, there are provided die-attach pastes having increased interfacial adhesion. Invention die-attach pastes include benzoxazine-containing thermosetting resin compositions.

In further aspects of the invention, there are provided methods for enhancing adhesive strength of thermosetting resin compositions and methods for enhancing adhesion of a substrate bound to a metallic surface by a thermosetting resin composition.

DETAILED DESCRIPTION OF THE INVENTION

In accordance with the present invention, there are provided benzoxazines having the following structure:

$$L\text{---}(Ar(Q_n)\underset{R_x}{|})_m$$

wherein:
L is an optional alkylene or siloxane linking moiety,
Ar is optionally substituted arylene,
Q is an oxazine ring or amine salt thereof having the structure:

$$\underset{R''_y}{\underset{|}{\overset{2\quad 3}{\underset{6\quad 5}{O}}}}\text{N---Sp---R'},$$

and is bonded to Ar in a fused manner at positions 5 and 6 of the oxazine ring,
wherein:
Sp is optional, and if present, is an optionally substituted $C_1$ to $C_6$ alkylene, oxyalkylene, thioalkylene, carboxyalkylene, amidoalkylene, or sulfonatoalkylene spacer,
n is 1 or 2,
m is optional, and if present, is 1 or 2,
x and y are each independently 0 to 4, and
wherein at least one of R, R', and R" is a polymerizable moiety.

As employed herein, "arylene" refers to aromatic groups having in the range of 6 up to 14 carbon atoms and "substituted arylene" refers to arylene groups further bearing one or more substituents selected from hydroxy, alkyl, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, nitrone, amino, amido, C(O)H, acyl, oxyacyl, carboxyl, carbamate, sulfonyl, sulfonamide, sulfuryl, and the like.

As employed herein, "alkylene" refers to divalent hydrocarbyl radicals having 1 up to 20 carbon atoms, preferably 2-10 carbon atoms, and "substituted alkylene" refers to alkylene moieties bearing one or more of the substituents as set forth above.

As employed herein, "oxyalkylene" refers to an alkylene moiety wherein one or more of the carbon atoms have been replaced by oxygen atoms, and "substituted oxyalkylene" refers to an oxyalkylene moiety further bearing one or more of the substituents as set forth above.

As employed herein, "thioalkylene" refers to an alkylene moiety wherein one or more of the carbon atoms have been replaced by sulfur atoms, and "substituted thioalkylene" refers to an thioalkylene moiety further bearing one or more of the substituents as set forth above.

As employed herein, "carboxyalkylene" refers to an alkylene moiety wherein one or more of the carbon atoms have been replaced by a carboxyl group, and "substituted carboxyalkylene" refers to a carboxyalkylene moiety further bearing one or more of the substituents as set forth above.

As employed herein, "amidoalkylene" refers to an alkylene moiety wherein one or more of the carbon atoms have been replaced by an amido group, and "substituted amidoalkylene" refers to an amidoalkylene moiety further bearing one or more of the substituents as set forth above.

As employed herein, "sulfonatoalkylene" refers to an alkylene moiety wherein one or more of the carbon atoms have been replaced by a sulfonato group, and "substituted sulfonatoalkylene" refers to a sulfonatoalkylene moiety further bearing one or more of the substituents as set forth above.

As employed herein, "polymerizable moiety" refers to any substituent that can participate in polymerization reaction, such as, for example, an addition polymerization or a condensation polymerization. As employed herein, addition polymerization refers to polymerization mechanisms such as free-radical polymerization, anionic polymerization, cationic polymerization, ring-opening polymerization, or coordinative polymerization. As employed herein, condensation polymerization refers to polymerizations such as siloxane polymerization.

In one aspect of the invention, the polymerizable moiety participates in an addition polymerization. Preferred addition polymerizable moieties include, for example, optionally substituted alkenyl, oxyalkenyl, alkynyl, cycloalkenyl, bicycloalkenyl, styryl, (meth)acrylate, itaconate, maleimide, vinyl ester, epoxy, cyanate ester, nitrile, diallyl amide, benzocyclobutene, aromatic propargyl ether, aromatic acetylene, oxazoline, and the like. Most preferred addition polymerizable moieties include alkenyl, oxyalkenyl, (meth)acrylate, maleimide, or cycloalkenyl.

As employed herein, "alkyl" refers to hydrocarbyl radicals having 1 up to 20 carbon atoms, preferably 2-10 carbon atoms; and "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, C(O)H, acyl, oxyacyl, carboxyl, carbamate, sulfonyl, sulfonamide, sulfuryl, and the like.

As employed herein, "alkenyl" refers to straight or branched chain hydrocarbyl groups having at least one carbon-carbon double bond, and having in the range of about 2 up to about 12 carbon atoms, and "substituted alkenyl" refers to alkenyl groups further bearing one or more substituents As employed herein, "alkoxy" refers to the moiety —O-alkyl-, wherein alkyl is as defined above, and "substituted alkoxy" refers to alkoxy groups further bearing one or more substituents as set forth above.

As employed herein, "alkynyl" refers to straight or branched chain hydrocarbyl groups having at least one carbon-carbon triple bond, and having in the range of about 2 up to about 12 carbon atoms, and "substituted alkynyl" refers to alkynylene groups further bearing one or more substituents as set forth above.

As employed herein, "cycloalkyl" refers to cyclic ring-containing groups containing in the range of about 3 up to about 8 carbon atoms, and "substituted cycloalkyl" refers to cycloalkyl groups further bearing one or more substituents as set forth above.

As employed herein, "cycloalkenyl" refers to cyclic ring-containing groups containing in the range of about 3 up to about 8 carbon atoms and having at least one carbon-carbon double bond, and "substituted cycloalkenyl" refers to cycloalkenyl groups further bearing one or more substituents as set forth above.

As employed herein, "aryl" refers to aromatic groups having in the range of 6 up to about 14 carbon atoms and "substituted aryl" refers to aryl groups further bearing one or more substituents as set forth above.

As employed herein, "heteroaryl" refers to aromatic groups containing one or more heteroatoms (e.g., N, O, S, or the like) as part of the ring structure, and having in the range of 6 up to about 14 carbon atoms.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

In another aspect of the invention, the polymerizable moiety participates in a condensation polymerization. Preferred condensation polymerizable moieties include, for example, siloxanes Invention benzoxazine monomers are preferably liquids and may optionally contain additional functionality depending on the specific application, such as, for example, alcohols, amines, silane esters, thiols, isocyanates, anhydrides, and the like.

In one embodiment, invention benzoxazines have the following structure:

$R_x$—Ar(Q)$_n$ 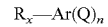

wherein:

Ar is optionally substituted arylene,

Q is an oxazine ring or amine salt thereof having the structure:

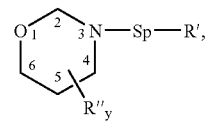

and is bonded to Ar in a fused manner at positions 5 and 6 of the oxazine ring,

Sp is optional, and if present, is a $C_1$ to $C_6$ alkylene oxyalkylene, thioalkylene, carboxyalkylene, amidoalkylene, or sulfonatoalkylene spacer, n is 1 or 2, x and y are each independently 1 to 4, and wherein at least one of R, R', or R" is a polymerizable moiety.

Invention benzoxazines may contain one or two oxazine rings per aryl ring, represented by the following exemplary structures A and B, respectively:

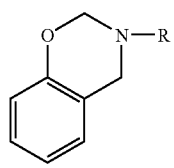

A

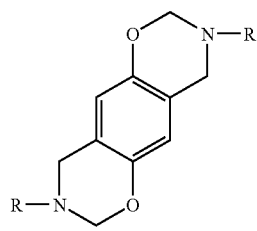

B

Presently preferred benzoxazines having the above exemplary structures include the following:

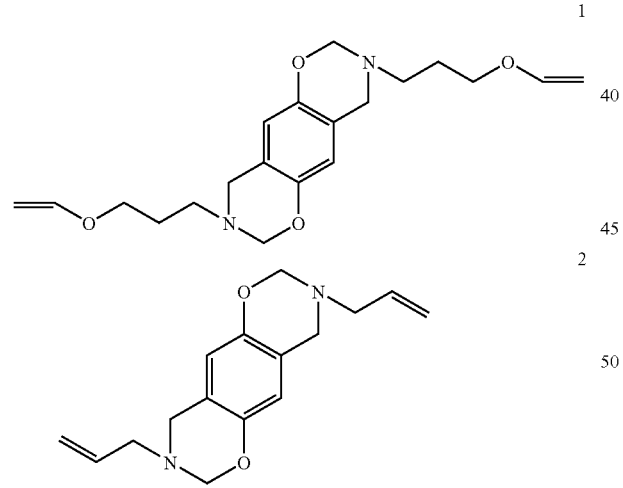

1

2

3

-continued

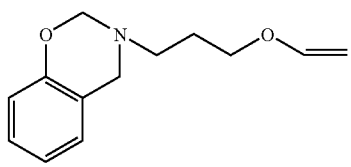

4

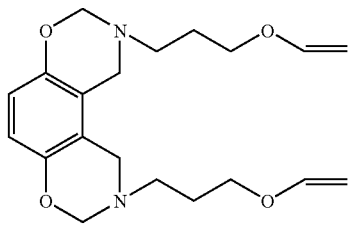

5

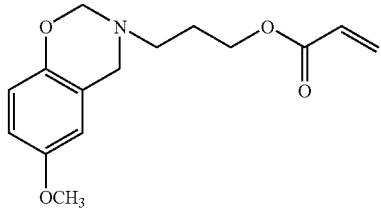

6

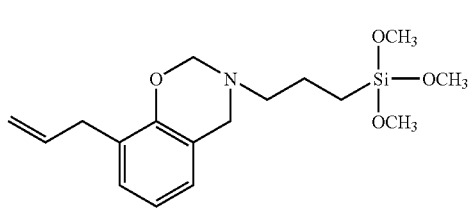

8

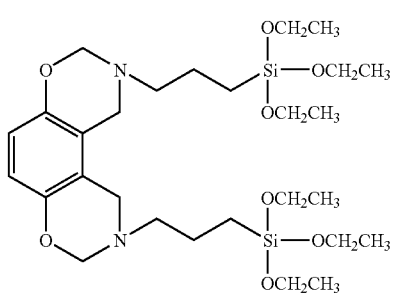

9

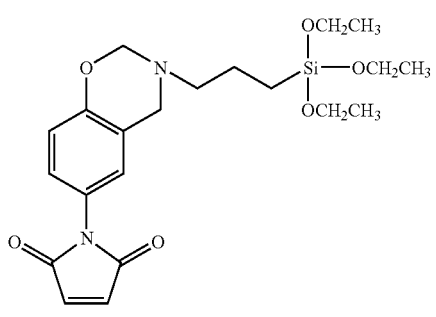

15

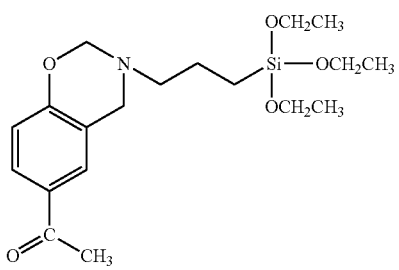

16

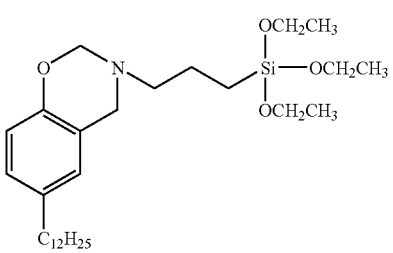

17

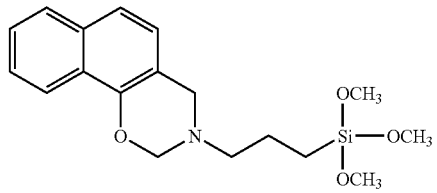

5

In another aspect, said optionally substituted arylene is naphthylene, represented by the following exemplary structure C:

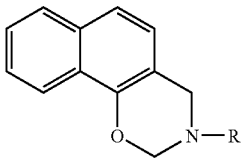

C

Presently preferred benzoxazines having exemplary structure C include the following:

In another aspect of the invention, benzoxazines contain an optional linker moiety L. A variety of groups are contemplated for use as a linker, such as, for example, alkylene or siloxane groups. The linking moiety can link benzoxazine groups in a variety of ways, e.g., via the aromatic rings or via the nitrogen atoms of the oxazine rings, as shown in the following exemplary structures D and E, respectively:

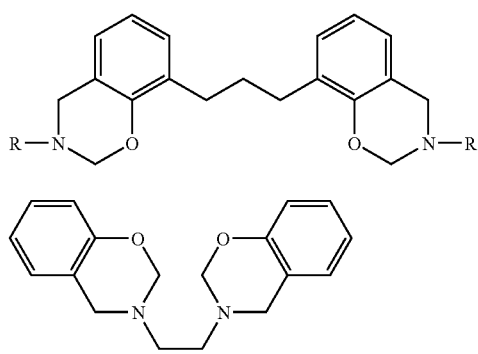

Benzoxazines containing optional linking groups L have the following exemplary structures:

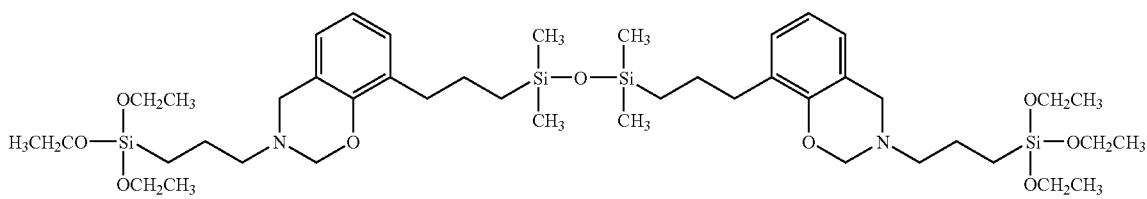

10

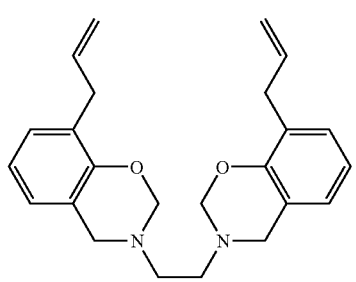

11

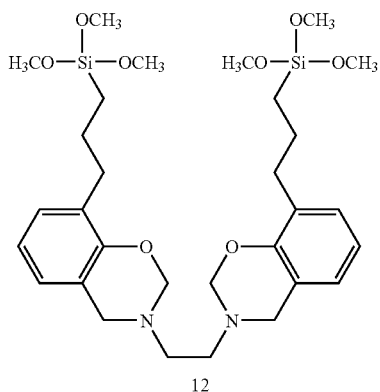

12

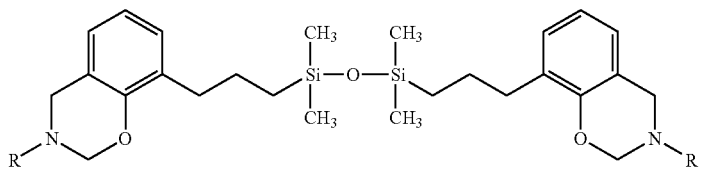

13 (R = t - Bu) and 14 (R = Ph)

Invention benzoxazines are readily prepared in one step from an aromatic alcohol, formaldehyde, and primary amine, as shown in Scheme 1:

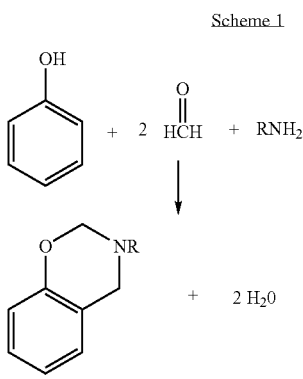

Functionality can be readily incorporated into invention benzoxazines by using a substituted aromatic alcohol and/or substituted primary amine in the synthesis outlined in Scheme 1.

In another aspect of the invention, there are provided thermosetting resin compositions containing one or more of the above described benzoxazines. Inventions compositions exhibit markedly increased adhesion to a variety of substrates, such as, for example, copper, aluminum, silicon, and the like. Thus, invention compositions are particularly useful for assembling microelectronic components.

Thermoset chemistries contemplated for use in the practice of the present invention include epoxy, cyanate ester, maleimide, acrylate, methacrylate, vinyl ether, styrenic, vinyl ester, propargyl ether, diallylamide, aromatic acetylene, benzocyclobutene, thiolene, maleate, oxazoline, itaconate, and the like, as well as combinations of any two or more thereof.

A presently preferred thermoset material contemplated for use in the practice of the present invention is maleimide. Maleimides contemplated for use in the practice of the present invention have the following structure:

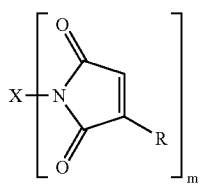

wherein:

m is 1-3, each R is independently hydrogen or lower alkyl, and

X is a saturated straight chain or branched chain alkyl, alkylene, or alkylene oxide, optionally containing saturated cyclic moieties as substituents on said alkyl, alkylene or alkylene oxide chain or as part of the backbone of the alkyl, alkylene or alkylene oxide chain.

Invention compositions exhibit significantly increased adhesive strength after incorporation of only small amounts of invention benzoxazines. Thus, invention benzoxazines are generally incorporated at levels in the range of about 0.5 up to about 25 wt % of the total thermoset monomers present in the composition. Presently preferred levels of incorporation are in the range of about 1 up to about 10 wt % of the total thermoset monomers present. Presently most preferred levels of incorporation are in the range of about 1 up to about 5 wt % of the total thermoset monomers present.

When invention benzoxazines are contemplated for use as components of free-radically cured thermosets, it is important to keep in mind that all benzoxazines contain a tertiary amine group. It is known that tertiary amines may inhibit free-radical curing reactions. Thus, to minimize the impact of tertiary amine groups on the free-radical cure, the tertiary amines can be converted to an amine salt by the addition of one equivalent of a suitable acid (see Scheme 2).

Scheme 2

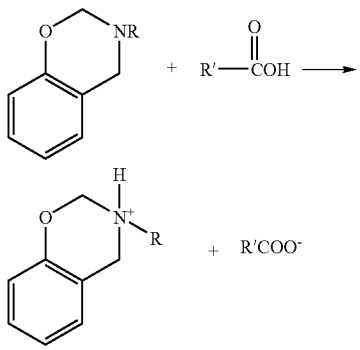

It is especially desirable to use an acid that is itself capable of participating in a free radical cure (i.e., R' in Scheme 2 is a moiety capable of polymerizing free-radically). Examples of acidic, free-radically-curable compounds that can be used to form amine salts include monobasic acids such as acrylic, methacrylic, 2-carboxyethyl acrylate, maleimidopropionic, maleimidocaproic, cinnamic, 4-styrenesulfonic, 4-vinylbenzoic, undecylenic, vinylsulfonic acids, and the like. Examples of dibasic acids that can be used for this purpose include maleic, furmaric, itaconic, vinylphosphonic acids, and the like.

An alternative method that may be used to reduce the free-radical cure inhibition of the tertiary amine is to oxidize the amine to an N-oxide (see Scheme 3).

Scheme 3

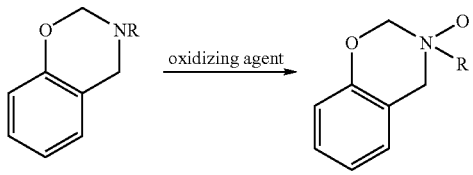

Conversion of the tertiary amine residues to N-oxides may be accomplished through the use of oxidizing agents such as peracetic acid, hydrogen peroxide, and the like. Procedures to perform this oxidation are well known to those familiar with the art.

In addition, it is of note that benzoxazines contemplated for use in the practice of the present invention need not necessarily crosslink with other thermoset materials in the composition during cure to provide beneficial properties. For example, incorporation of benzoxazine compounds that contain no free-radically polymerizable group into a peroxide catalyzed, maleimide-based thermosetting composition remarkably increases the tensile, room temperature bond strength to copper and aluminum. Use of invention benzoxazines is also shown herein to be useful as a means to retain (or in some cases improve) the adhesion of compositions subjected to extended high temperature storage.

Optionally, invention compositions can further contain one or more of the following additional components: anti-oxidants, bleed control agents, one or more fillers, inert (i.e., nonreactive) diluents, reactive diluents, coupling agents, adhesion promoters, flexibilizers, dyes, pigments, and the like.

Anti-oxidants contemplated for optional use in the practice of the present invention include hindered phenols (e.g., BHT (butylated hydroxytoluene), BHA (butylated hydroxyanisole), TBHQ (tertiary-butyl hydroquinone), 2,2'-methylenebis(6-tertiarybutyl-p-cresol), and the like), hindered amines (e.g., diphenylamine, N,N'-bis(1,4-dimethylpentyl-p-phenylene diamine, N-(4-anilinophenyl) methacrylamide, 4,4'-bis($\alpha,\alpha$-dimethylbenzyl) diphenylamine, and the like), phosphites, and the like. When used, the quantity of antioxidant typically falls in the range of about 100 up to about 2000 ppm, relative to the weight of the base formulation.

Bleed control agents contemplated for optional use in the practice of the present invention include cationic surfactants, tertiary amines, tertiary phosphines, amphoteric surfactants, polyfunctional compounds, and the like, as well as mixtures of any two or more thereof. Those of skill in the art recognize that the quantity of bleed control agent employed in the practice of the present invention can vary widely, typically falling in the range of about 0.1 up to about 10 wt %, relative to the weight of the base formulation.

Fillers contemplated for optional use in the practice of the present invention may optionally be conductive (electrically and/or thermally). Electrically conductive fillers contemplated for use in the practice of the present invention include, for example, silver, nickel, gold, cobalt, copper, aluminum, graphite, silver-coated graphite, nickel-coated graphite fillers, alloys of such metals, and mixtures thereof, and the like. Both powder and flake forms of filler may be used in the die-attach paste compositions of the present invention. Preferably, the flake has a thickness of less than about 2 microns, with planar dimensions of about 20 to about 25 microns. Flake contemplated for use herein preferably has a surface area of about 0.15 to 5.0 $m^2/g$ and a tap density of about 0.4 up to about 5.5 g/cc. It is presently preferred that powder employed in the practice of the invention has a diameter in the range of about 0.5 up to about 15 microns.

Thermally conductive fillers contemplated for optional use in the practice of the present invention include, for example, aluminum nitride, boron nitride, silicon carbide, diamond, graphite, beryllium oxide, magnesia, silica, alumina, and the like. Preferably, the particle size of these fillers will be about 20 microns. If aluminum nitride is used as a filler, it is preferred that it be passivated via an adherent, conformal coating (e.g., silica, or the like).

Electrically and/or thermally conductive fillers are optionally (and preferably) rendered substantially free of catalytically active metal ions by treatment with chelating agents, reducing agents, nonionic lubricating agents, or mixtures of such agents. Such treatment is described in U.S. Pat. No. 5,447,988, which is incorporated by reference herein in its entirety.

Optionally, a filler may be used that is neither an electrical nor thermal conductor. Such fillers may be desirable to impart some other property such as reduced dielectric constant, improved toughness, increased hydrophobicity, and the like. Examples of such fillers include perfluorinated hydrocarbon polymers (i.e., TEFLON™), thermoplastic polymers, thermoplastic elastomers, mica, fused silica, and the like.

While the use of inert diluents is not excluded from the practice of the present invention, it is generally preferred that compositions according to the invention remain substantially free of solvent, so as to avoid the potentially detrimental effects thereof, e.g., creation of voids caused by solvent escape, the environmental impact of vaporized solvent, the redeposifion of outgassed molecules on the surface of the article, and the like. When used, suitable inert diluents include dimethylformamide, dimethylacetamide, N-methylpyrrolidone, toluene, xylene, methylene chloride, tetrahydrofuran, glycol ethers, methyl ethyl ketone or monoalkyl or dialkyl ethers of ethylene glycol, polyethylene glycol, propylene glycol, polypropylene glycol, and the like. When used, inert diluents are typically present in the range of about 10 up to about 40 wt %, relative to the weight of the base formulation.

Reactive diluents contemplated for optional use in the practice of the present invention include any reactive diluent which, in combination with the maleimide-based benzoxazine-containing formulations described herein, forms a thermosetting resin composition. Such reactive diluents include acrylates and methacrylates of monofunctional and polyfunctional alcohols, ethylenically unsaturated compounds, styrenic monomers (i.e., ethers derived from the reaction of vinyl benzyl chlorides with mono-, di-, or trifunctional hydroxy compounds), and the like. When used, reactive diluents are typically present in the range of about 5 up to about 15 wt %, relative to the weight of the base formulation.

In a particular aspect, compositions according to the invention optionally further contain in the range of about 0.1 up to about 10 wt % of at least one coupling agent, based on the total weight of the composition. Coupling agents contemplated for use in the practice of the present invention include silicate esters, metal acrylate salts, titanates or compounds containing a co-polymerizable group and a chelating ligand.

As employed herein, the term "adhesion promoters" refers to components (other than invention compounds) which have pendant acid or latent acid groups that can increase adhesion. An example is the Ricon R-130 20% maleated (Ricon Resins, Inc., Grand Junction, Colo.), a polybutadiene with anhydride groups that can react with a surface to increase adhesion. When present, adhesion promoters are typically present in the range of about 5 up to about 30 wt %, relative to the weight of the base formulation.

Flexibilizers contemplated for optional use in the practice of the present invention include branched polyalkanes or polysiloxanes that lower the $T_g$ of the formulation. An example of such a material would be polybutadienes such as the Ricon R-130 as described hereinabove. When present, flexibilizers are typically present in the range of about 15 up to about 60 wt %, relative to the weight of the base formulation.

Dyes contemplated for optional use in the practice of the present invention include nigrosine, Orasol blue GN, phthalocyanines, and the like. When used, organic dyes in relatively low amounts (i.e., amounts less than about 0.2 wt %) provide contrast.

Pigments contemplated for optional use in the practice of the present invention include any particulate material added solely for the purpose of imparting color to the formulation, e.g., carbon black, metal oxides (e.g., $Fe_2O_3$, titanium oxide), and the like. When present, pigments are typically present in the range of about 0.5 up to about 5 wt %, relative to the weight of the base formulation.

Those of skill in the art recognize that many different electronic packages would benefit from preparation using the invention compositions described herein. Examples of such packages include ball grid arrays, super ball grid arrays, IC memory cards, chip carriers, hybrid circuits, chip-on-board, multi-chip modules, pin grid arrays, chip size packages (CSPs), and the like. Thus, in a further aspect of the invention, there are provided die-attach pastes comprising invention compositions and optionally, a filler. Preferably, invention die-attach pastes comprise in the range of about 10 up to about 80 wt % of invention composition and in the range of about 20 up to about 90 wt % of a filler.

Invention compositions and die-attach pastes are particularly useful for enhancing the adhesion of a substrate to a metallic surface. In a particular aspect, the substrate is a semiconductor die, and the metallic surface is copper.

In still further aspects of the invention, there are provided methods for enhancing adhesive strength of a thermosetting resin composition and enhancing adhesion of a substrate bound to a metallic surface by a thermosetting resin composition, wherein the methods comprise incorporating an effective amount of one or more invention compounds into the composition. In a preferred embodiment of this aspect of the invention, the metallic surface is copper.

In yet another aspect of the invention, there is provided a method for adhesively attaching a substrate to a metallic surface, wherein the method comprises curing a die-attach paste positioned between the substrate and the metallic surface, wherein the die-attach paste comprises one or more invention compounds. In a preferred embodiment of this aspect of the invention, the substrate is a semiconductor die and the metallic surface is a lead frame. In an especially preferred embodiment, the lead frame is a copper lead frame.

The invention will now be described in greater detail by reference to the following non-limiting examples.

For each of the following Examples, the formation of the benzoxazine was confirmed by IR spectroscopy, wherein the disappearance of the characteristic —OH stretch of the phenol starting material was accompanied by the observance of the characteristic R—O—R stretch of the oxazine ring at 1080 cm$^{-1}$.

EXAMPLE 1

Benzoxazine 1. Hydroquinone (8.23 grams, 75 mmole), 3-amino-1-propanol vinyl ether (15.1 grams, 150 mmole), and toluene (100 mL) were placed in a 250 mL round bottom flask. Paraformaldehyde (9.0 grams, equivalent to 300 mmole of formaldehyde) was then added to the flask. The flask was then equipped with a magnetic stir bar, a Dean-Stark trap, and condenser. The mixture was stirred and heated to reflux under an argon blanket. A total of 5.2 milliliters (96% of theory) of water was collected in the trap after two hours reflux. The reaction mixture had turned black by this point. The toluene reaction solution was washed with two 50 mL aliquots of 5% aqueous sodium hydroxide, followed by one 50 mL aliquot of water. The toluene solution was passed over a bed of neutral alumina and then evaporated to yield 3.8 grams (14% of theory) of a viscous, light brown liquid.

EXAMPLE 2

Benzoxazine 2. Hydroquinone (8.23 g, 75 mmol), allylamine (8.57 g, 150 mmol) and toluene (100 mL) were placed in a 250 mL flask. Paraformaldehyde (9.0 grams, equivalent to 300 mmole formaldehyde) was added along with a magnetic stir bar. The flask was equipped as described in Example 1 and brought to reflux. The full theoretical amount of water was collected within forty-five minutes of reflux. The toluene solution was washed with six 25 ml portions of 5% aqueous sodium hydroxide, and three 30 ml aliquots of water. The toluene solution was then dried over anhydrous magnesium sulfate and then passed over 26 grams of activated, neutral alumina. The toluene was removed to yield 11.0 grams (54% of theory) of a red, semi-solid material.

EXAMPLE 3

Benzoxazine 3. A 500 mL flask was equipped with a magnetic stirring bar and a Dean-Stark trap. This assembly was then charged with hydroquinone (33.0 g, 300 mmole), 1-amino-2-propanol (45.0 g, 600 mmole), and about 38 g (1260 mmol) of paraformaldehyde. Approximately 300 mL of toluene was added to the flask and the mixture was heated to reflux. As the reaction proceeded all of the reactants dissolved and a homogeneous solution formed. After one hour of reflux at 110° C., about 22 mL of water was collected in the Dean-Stark trap. The solution was allowed to cool to room temperature before proceeding to the next step. At this point a bis-benzoxazine intermediate with two pendent alcohol groups should have formed in the reaction vessel. No attempt was made to isolate the intermediate, instead this diol was converted to a diacrylate. The solution was placed in an ice bath at 0° C., along with 100 g (1 mole) of triethylamine. The acrylation was achieved by the dropwise addition of acryloyl chloride (60 g, 660 mmoles) over a period of thirty minutes. Following the addition, the dark solution was allowed to stir overnight at room temperature. The reaction was worked up by placing it into a separatory funnel and washing twice with water, followed by a sodium bicarbonate wash. The solution was dried over magnesium sulfate and filtered through a small bed of silica gel. The solvent was removed under reduced pressure to obtain 35 g (28% yield) of an orange colored liquid. The IR spectra (1726 cm$^{-1}$) indicated that the acrylate functional group was present.

EXAMPLE 4

Benzoxazine 4. This compound was made according to the method outlined in Example 3, by combining phenol (28 g, 300 mmole), 3-amino-1-propanol vinyl ether (30 g, 300 mmole), and paraformaldehyde (19.5 g, (650 mmole) in a 500 ml flask. The water condensate was removed using toluene as the azeotrope solvent. The product was worked-up to obtain 50 g (76% yield) of a light yellow, low viscosity liquid.

EXAMPLE 5

Benzoxazine 5. A 500 mL flask was charged with resorcinol (33 g, 300 mmol), 3-amino-1-propanol vinyl ether (61 g, 600 mmol), and paraformaldehyde (38 g, 1260 mmol). Approximately 200 g of toluene was added and the mixture was heated to reflux. Reflux continued until water ceased to collect in the trap (about one hour). The reaction mixture was then cooled to room temperature. A large volume of solid byproduct formed in the reaction vessel. The toluene solution was decanted from the solid, and the remaining solid was washed with extra toluene. All of the toluene fractions were combined in a separatory funnel. The toluene solution was washed with a 5% NaOH solution, followed by a saturated NaCl solution. The toluene solution was dried with magnesium sulfate, and filtered over a small bed of neutral alumina. Removal of the solvent under reduced pressure produced about 50 g of an orange colored liquid (46% yield).

EXAMPLE 6

Benzoxazine 6. A 500 mL flask was charged with 4-methoxyphenol (12.4 g, 100 mmol), 3-amino-1-propanol (7.5 g, 100 mmol), and paraformaldehyde (6.4 g, 213 mmol). Toluene (200 g) was added to the flask and the mixture was heated to reflux for one hour, during which time 3.8 mL of water was collected in a Dean-Stark trap. The solution was cooled to 0° C., and triethylamine (23 g, 227 mmol) was added to the flask. This was followed by the drop-wise addition of acryloyl chloride (11 g, 125 mmol). The solution was allowed to stir overnight at room temperature. The product was worked up in a similar fashion as described in previous examples. About 20 g (72% yield) of a low viscosity, orange liquid was recovered.

EXAMPLE 7

Benzoxazine 7. This compound was prepared according to the method described in previous examples using 3-aminopropyltrimethoxysilane (17.9 g, 100 mmole), paraformaldehyde (6.3 g, 210 mmole), 1-naphthol (14.4 g, 100 mmole), and toluene (200 ml). The final product was obtained as a viscous liquid. The yield was 80% of theory.

EXAMPLE 8

Benzoxazine 8. This compound was prepared according to the method described in the previous examples using 3-aminopropyltrimethoxysilane (17.9 g, 100 mmole), paraformaldehade (6.3 g, 210 mmole), 2-allyl-phenol (13.4 g, 0.1 mmole), and toluene (200 ml). The final product was obtained as a slightly yellow, mobile liquid. The yield was 94% of theory.

EXAMPLE 9

Benzoxazine 9. This compound was prepared according to the method described previously using 3-aminopropyltriethoxysilane (22.1 g, 100 mmole), paraformaldehade (6.3 g, 210 mmole), hydroquinone (5.5 g, 50 mmole), and toluene (150 ml). The final product was a viscous liquid. The yield was 65% of theory.

EXAMPLE 10

Before synthesis of benzoxazine 10, the precursor tetramethyldisiloxane-bridged-bisphenol was prepared. A 500 mL round bottom flask containing a magnetic stir bar was charged with 2-allylphenol (67.1 g, 500 mmole); 1,1,3,3-tetramethyldisiloxane (33.6 g, 250 mmole) and toluene (100 ml). Two drops of Platinum catalyst (Platinum-divinyl tetramethyldisiloxane complex in xylene, from UCT) were added while the mixture was stirred at room temperature. The reaction mixture was stirred another two hours at room temperature (until the absorption around 2200 cm$^{-1}$ in FTIR spectrum had completely disappeared from the reaction product). This mixture was then passed through a thin layer of silica gel and the solvent was removed by rotary evaporation. The product was a pale yellow liquid. The recovered yield of the desired bisphenol was 98% of theory.

Benzoxazine 10. A 500 mL round bottom flask was charged with 3-aminopropyltriethoxysilane (44.2 g, 200 mmol), paraformaldehyde (15.0 g, 500 mmole), siloxane bridged bisphenol (26.8 g, 100 mmole, prepared as described in Example 10A), and toluene (200 ml). A magnetic stir bar was added to the flask, which was fitted with a Dean-Stark trap and condenser. The reaction mixture was heated to reflux for 4.0 hours while stirring. A total of 7.2 ml (400 mmole) of water was collected. The reaction mixture was allowed to cool to room temperature and then passed through a thin layer of silica gel. The toluene solvent was removed by rotary evaporation and the residue remaining in the flask was sparged with nitrogen gas for four hours while the flask was maintained at 60° C. The final product was a slightly red, moderately viscous liquid. The yield of this bisbenzoxazine was 80% of theory.

EXAMPLE 11

Benzoxazine 11. This compound was prepared according to the method described in the previous examples from ethylene diamine (6.0 g, 100 mmole), paraformaldehade (12.6 g, 420 mmole), 2-allyl-phenol (26.8 g, 200 mmole), and toluene (200 ml). The final product was obtained as a viscous liquid. The yield was 92% of theory.

EXAMPLE 12

Benzoxazine 12. A. This compound was prepared in two steps starting from a reaction mixture comprising trimethoxysilane (4.6 g, 40 mmole), 2-allyl-phenol (5.2 g, 40 mmole), platinum catalyst (2 drops of platinum-divinyl tetramethyldisiloxane complex in xylene, from UCT,) and toluene (20 ml). This intermediate hydrosilation product was obtained as a viscous liquid. The yield was 80% of theory.

The desired benzoxazine was prepared from the reaction of ethylene diamine (0.9 g, 15 mmole), 2-[(trimethoxysilyl)propyl]phenol (7.68 g, 30 mmole, prepared as described in Example 12A), paraformaldehyde (2.1 g, 70 mmole), and toluene (20 ml). The final product was a viscous liquid. The yield was 65% of theory.

EXAMPLE 13

Benzoxazine 13. A 500 mL three-neck round-bottom flask with a stir-bar was charged with tert-butylamine (14.6 g, 200 mmole), paraformaldehyde (15.0 g, 500 mmole), siloxane-bridged-bisphenol (26.8 g, 0.1 mol, prepared by the procedure described in Example 10), and toluene (200 mL) were placed into a 500 mL. The flask was connected to a Dean-Stark trap and condenser and the reaction mixture was heated to reflux for 4.0 hours while stirring. A total of 7.2 ml (400 mmol) of water was collected. The reaction mixture was allowed to cool to room temperature and passed through a thin layer of silica gel. The toluene was removed by rotary evaporation and the residue was sparged with nitrogen gas for five hours at 60° C. The final product was a fairly mobile, clear, red liquid. The yield was 78% of theory.

EXAMPLE 14

Benzoxazine 14. This compound was prepared according to the method used for the previous examples by combining the siloxane-bridged-bisphenol (26.8 g, 100 mmole, made according to the procedure described in Example 10), aniline (18.6 g, 200 mmole) paraformaldehyde (15.0 g, 500 mmole), and toluene (200 ml). The final product was a yellow semi-solid. The yield of this product was 70% of theory.

EXAMPLE 15

Benzoxazine 15. This compound was prepared according to the method used for the previous examples by combining 4-maleimidophenol (18.9 g, 100 mmol), 3-aminopropyltriethoxysilane (22.1 g, 100 mmol), paraformaldehyde (6.3 g, 210 mmol), and toluene (150 mL). The final product was a highly viscous red liquid. The yield was 37%.

EXAMPLE 16

Benzoxazine 16. This compound was prepared according to the method used for the previous examples by combining 4-hydroxyacetophenone (13.6 g, 100 mmol), 3-aminopropyltriethoxysilane (22.1 g, 100 mmol), paraformaldehyde (6.3 g, 210 mmol), and toluene (150 mL). The final product was a clear, almost colorless liquid. The yield was 55%.

EXAMPLE 17

Benzoxazine 17. This benzoxazine was prepared from 4-dodecylphenol (26.2 g, 100 mmol), 3-aminopropyltriethoxysilane (22.1 g, 100 mmol), paraformaldehyde (6.3 g, 210 mmol), and toluene (150 mL). The method to prepare this compound was the same as that used to make the previous benzoxazines. The final product was a clear, faint yellow liquid. The yield was 92%.

EXAMPLE 18

Each of the benzoxazine compounds described above were tested for their effect on adhesion at various concentration levels in a bismaleimide liquid adhesive. The concentration levels tested for the benzoxazine compounds are set forth in Table 1. The base monomer for these tests was the bismaleimide of the dimer diamine 1,20-bismaleimido-10,11-dioctyl-eicosane, which likely exists in admixture with other isomeric species produced by thermal reaction of oleic acids, or like reactions as described in U.S. Pat. Nos. 6,034,194 and 6,034,195. The mixtures were catalyzed to cure by the addition of 2 wt % dicumyl peroxide initiator. The mixture containing only the liquid BMI and catalyst served as a control in all of these tests.

Adhesion was evaluated using a tensile test method. Aluminum studs (with a head diameter of 280 mils) were attached to clean copper slugs (1000×400×150 mils) using each of the test formulations as well as a control. Ten of these test assemblies were constructed for each of the mixtures. The adhesive-test assemblies were processed by heating them in an air-circulating oven set at 200° C. for thirty minutes. The parts were allowed to cool to room temperature and the adhesive strength was determined using a Sebastian III tensile tester. The adhesion test results (pounds force) were converted to pounds per square inch based on the contact area of the aluminum stud. All values shown in Table 1 are averages for the ten test adhesive-test assemblies that were prepared for each mixture. Several tests were required to collect the data shown in Table 1. The control adhesion was therefore useful to normalize the test results with respect to day to day variations in the cure conditions. The percent adhesion enhancement for each of the benzoxazine test additives was determined according to the equation:

$$\% \text{ enhancement} = [(\text{test mixture adhesion} \div \text{control adhesion}) - \text{control adhesion}] \times 100$$

TABLE 1

Impact of Benzoxazine Modifiers on Tensile Adhesion

| Benzoxazine Compound | % Added to Mixture | Adhesion (PSI) | Control Adhesion (PSI) | Adhesion Enhancement (%) |
|---|---|---|---|---|
| 1 | 2 | 967 | 319 | 203 |
|   | 4 | 1361 | 319 | 327 |
|   | 6 | 1414 | 319 | 343 |
|   | 8 | 1244 | 319 | 290 |
| 2 | 2 | 737 | 241 | 206 |
|   | 5 | 335 | 241 | 39 |
| 3 | 2 | 415 | 264 | 57 |
|   | 5 | 679 | 264 | 157 |
| 4 | 4 | 901 | 235 | 283 |
|   | 8 | 914 | 314 | 191 |

TABLE 1-continued

Impact of Benzoxazine Modifiers on Tensile Adhesion

| Benzoxazine Compound | % Added to Mixture | Adhesion (PSI) | Control Adhesion (PSI) | Adhesion Enhancement (%) |
|---|---|---|---|---|
| 5 | 4 | 757 | 235 | 222 |
|   | 8 | 977 | 314 | 211 |
| 6 | 5 | 831 | 460 | 81 |
| 7 | 4 | 1294 | 387 | 234 |
| 8 | 4 | 1553 | 387 | 301 |
| 9 | 4 | 1369 | 358 | 282 |
| 10 | 4 | 1628 | 358 | 355 |
| 11 | 4 | 991 | 326 | 204 |
|   | 8 | 917 | 326 | 181 |
| 12 | 4 | 512 | 326 | 57 |
| 13 | 4 | 680 | 178 | 282 |
| 14 | 4 | 620 | 178 | 248 |
| 15 | 4 | 807 | 293 | 175 |
| 16 | 4 | 852 | 293 | 191 |
| 17 | 4 | 1171 | 293 | 300 |

It is readily apparent from the results summarized in Table 1 that every invention significantly improved adhesion versus the control. The amount of invention compound sufficient to impart improved adhesion was quite low. In fact, the greatest benefit, in many cases, was obtained with 5 wt % or less of benzoxazine added to the composition. The addition of more than 5 wt % invention compounds (in most of the cases where higher levels were also evaluated) didn't appear to dramatically further improve adhesion.

EXAMPLE 19

A study was carried out using two of the benzoxazines described above in which the tertiary amine groups of were converted to the corresponding pseudo quaternary ammonium compounds. Benzoxazine 4 was reacted with one equivalent of maleimidocaproic acid. Benzoxazine 16 was reacted with one equivalent of acrylic acid. These salts were then tested in the same fashion (again with ten parts in each leg of the test) described earlier. The adhesion results for these two pseudo quaternary ammonium benzoxazine additives are shown in Table 2.

TABLE 2

Impact of Benzoxazine Salts on Tensile Adhesion Performance

| Benzoxazine Compound Salt | Percent Added to Mixture | Adhesion (PSI) | Control Adhesion (PSI) | Adhesion Enhancement (%) |
|---|---|---|---|---|
| 4 | 4 | 1128 | 399 | 180 |
| 16 | 4 | 1189 | 251 | 374 |

The absolute adhesion values were higher for both of these compounds in the salt form compared to the earlier tensile adhesion test results (Table 1) for their free-base benzoxazine equivalents. However, the control for the salt version of compound 4 was also higher in this test, so the percent adhesion enhancement was actually reduced compared to the parent benzoxazine. The salt version of Benzoxazine 16 was significantly higher than that of the original compound in terms of both absolute and normalized adhesion.

EXAMPLE 20

Another study was conducted to determine the thermal aging properties of adhesive mixtures containing one of the invention benzoxazine additives. The thermal resistance test is considered a useful measure of the extent to which an adhesive will perform after exposure to high temperature assembly processes (such as post-mold-bake of electronic material encapsulants). The study was conducted using Benzoxazine 1. Ten parts were again assembled for each leg of the test. The tensile adhesion results at time zero and after sixteen hours at 200° C. are shown in Table 3.

TABLE 3

Impact of Oven Aging on Mixtures Containing Benzoxazine 1

| Hours Aging at 200° C. | Percent Added to Mixture | Adhesion (PSI) | Control Adhesion (PSI) | Adhesion Enhancement (%) |
|---|---|---|---|---|
| 0 | 4 | 1361 | 319 | 327 |
|   | 8 | 1244 | 319 | 290 |
| 16 | 4 | 1387 | 177 | 684 |
|   | 8 | 1657 | 177 | 836 |

The absolute adhesion values were improved for the Benzoxazine 1 test mixtures after the sixteen hour thermal aging. This result is even more remarkable in light of the poor retained adhesion for the control after the thermal aging. The addition of low levels of benzoxazine additives, therefore, improves the high temperature thermal resistance of thermoset adhesives, mold compounds and liquid encapsulants.

While the invention has been described in detail with reference to certain preferred embodiments thereof, it will be understood that modifications and variations are within the spirit and scope of that which is described and claimed.

What is claimed is:

1. A thermosetting resin composition for adhering materials with dissimiliar coefficients or thermal expansion, consisting essentially of:
   a) a benzoxazine compound in liquid form at room temperature,
   b) one or more thermoset compounds selected from the group consisting of epoxy, cyanate ester, maleimide, acrylate, methacrylate, vinyl ether, styrenic, vinyl ester, propargyl ether, diallylamide, aromatic acetylene, benzocyclobutene, thiolenes, maleate, oxazoline, and itaconate,
   c) optionally, one or more anti-oxidants, bleed control agents, fillers, diluents, coupling agents, adhesion promoters, flexibilizers, dyes and pigments, and
   d) a cure initiator.

2. A method for enhancing adhesive strength of a thermosetting resin composition between materials with dissimiliar coefficients of thermal expansion, said method consisting essentially of the step of:
   incorporating an effective amount of a benzoxazine compound in liquid form at room temperature into a composition comprising one or more thermoset compounds selected from the group consisting of epoxy, cyanate ester, maleimide, acrylate, methacrylate, vinyl ether, styrenic, vinyl ester, propargyl ether, diallylamide, aromatic acetylene, benzocyclobutene, thiolenes, maleate, oxazoline, and itaconate; optionally, one or more anti-oxidants, bleed control agents, fillers, diluents, coupling agents, adhesion promoters, flexibilizers, dyes and pigments, and a cure initiator.

3. A method according to claim 2, wherein one of the materials with dissimiliar coefficients of thermal expansion has a metallic surface to which the thermosetting resin composition is adhered.

4. A method according to claim 3, wherein said metallic surface is copper.

5. A method for adhesively attaching a first substrate to a second substrate, said method comprising the steps of
providing the first substrate,
providing the second substrate,
providing a thermosetting resin composition according to claim 2 positioned between said first and second substrates and curing the composition therebetween.

6. A method according to claim 5, wherein said first substrate is a semiconductor die and said second substrate is circuit board.

7. A method according to claim 5, wherein said first substrate is a semiconductor die and said second substrate has a metallic surface, which is a lead frame.

8. A method according to claim 7, wherein said lead frame is a copper lead frame.

9. A composition according to claim 1, wherein said maleimide is in liquid form.

10. A composition according to claim 1, wherein said filler is conductive.

11. A composition according to claim 1, wherein said filler is electrically conductive.

12. A composition according to claim 1, wherein said filler is thermally conductive.

13. A composition according to claim 1, wherein said maleimide has the structure:

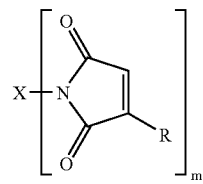

wherein:
m is 1-3,
each R is independently hydrogen or lower alkyl, and
X is a straight chain alkyl, alkylene, or alkylene oxide, or branched chain alkyl, alkylene or alkylene oxide, optionally containing cyclic moieties as substituents on said alkyl, alkylene or alkylene oxide chain or as part of the backbone of the alkyl, alkylene or alkylene oxide chain.

* * * * *